(12) United States Patent
Hewson et al.

(10) Patent No.: US 11,446,444 B2
(45) Date of Patent: Sep. 20, 2022

(54) DOSE DELIVERY MECHANISM

(71) Applicant: NORTON HEALTHCARE LIMITED, West Yorkshire (GB)

(72) Inventors: Karl James Hewson, Cambridgeshire (GB); George Bostock, Cambridgeshire (GB); George Robert Michael Savell, Cambridgeshire (GB)

(73) Assignee: Norton Healthcare Limited, Castleford (GB)

( * ) Notice: Subject to any disclaimer, the term of this patent is extended or adjusted under 35 U.S.C. 154(b) by 14 days.

(21) Appl. No.: 16/332,034

(22) PCT Filed: Sep. 11, 2017

(86) PCT No.: PCT/EP2017/072772
§ 371 (c)(1),
(2) Date: Mar. 11, 2019

(87) PCT Pub. No.: WO2018/046733
PCT Pub. Date: Mar. 15, 2018

(65) Prior Publication Data
US 2019/0358407 A1   Nov. 28, 2019

(30) Foreign Application Priority Data
Sep. 12, 2016   (GB) ...................................... 1615446

(51) Int. Cl.
| A61M 5/315 | (2006.01) |
| A61M 5/20 | (2006.01) |
| A61M 5/24 | (2006.01) |
| A61M 5/31 | (2006.01) |

(52) U.S. Cl.
CPC ...... A61M 5/31541 (2013.01); A61M 5/2033 (2013.01); A61M 5/24 (2013.01);
(Continued)

(58) Field of Classification Search
CPC .......... A61M 5/31541; A61M 5/31583; A61M 5/2033; A61M 5/24; A61M 5/31553;
(Continued)

(56) References Cited

U.S. PATENT DOCUMENTS

| 7,828,779 B2 | 11/2010 | Kirchhofer et al. |
| 2003/0160072 A1* | 8/2003 | Geiser ............... A61M 5/31551 222/327 |

(Continued)

FOREIGN PATENT DOCUMENTS

| FR | 2531879 A1 | 2/1984 |
| WO | 2008/101829 A1 | 8/2008 |

(Continued)

OTHER PUBLICATIONS

International Search Report and Written Opinion PCT/EP2017/072772, dated Dec. 8, 2017, 15 pages.

*Primary Examiner* — Amber R Stiles
*Assistant Examiner* — Avery Smale
(74) *Attorney, Agent, or Firm* — BakerHostetler

(57) ABSTRACT

An injection device comprises a housing having a first longitudinal axis (L). The injection device further comprises a medicament cartridge holder and a drive assembly including a drive shaft. The drive shaft is arranged around the first longitudinal axis. The drive assembly is capable of providing an axial force for ejecting a dose of medicament from the injection device. The medicament cartridge holder and at least part of said drive assembly are arranged around a second longitudinal axis (LC) which is substantially parallel to but offset from the first longitudinal axis.

21 Claims, 20 Drawing Sheets

(52) U.S. Cl.
CPC .... *A61M 5/31553* (2013.01); *A61M 5/31585* (2013.01); *A61M 2005/3126* (2013.01)

(58) Field of Classification Search
CPC ...... A61M 5/31585; A61M 2005/3126; A61M 5/3157; A61M 5/31593; A61M 5/31511; A61M 5/3129; A61M 5/31535; A61M 5/20; A61M 2005/2073; A61M 5/31501; A61M 5/31576; A61M 5/315
See application file for complete search history.

(56) References Cited

U.S. PATENT DOCUMENTS

2009/0299328 A1* 12/2009 Mudd ............... A61M 5/31575
604/506

2014/0088553 A1* 3/2014 Hetherington .... A61M 5/31585
604/506
2015/0352288 A1* 12/2015 Andersen .......... A61M 5/31528
604/134

FOREIGN PATENT DOCUMENTS

| WO | WO-2008101829 A1 * | 8/2008 | ........ A61M 5/31565 |
|---|---|---|---|
| WO | 2011/039207 A1 | 4/2011 | |
| WO | 2011/136718 A1 | 11/2011 | |
| WO | 2013/178372 A1 | 12/2013 | |
| WO | 2014/166916 A1 | 10/2014 | |
| WO | 2014/166922 A2 | 10/2014 | |
| WO | WO-2014166922 A2 * | 10/2014 | ........ A61M 5/31553 |
| WO | 2015/007820 A1 | 1/2015 | |
| WO | 2015/032780 A1 | 3/2015 | |
| WO | 2016/055438 A1 | 4/2016 | |
| WO | 2016/091978 A1 | 6/2016 | |

* cited by examiner

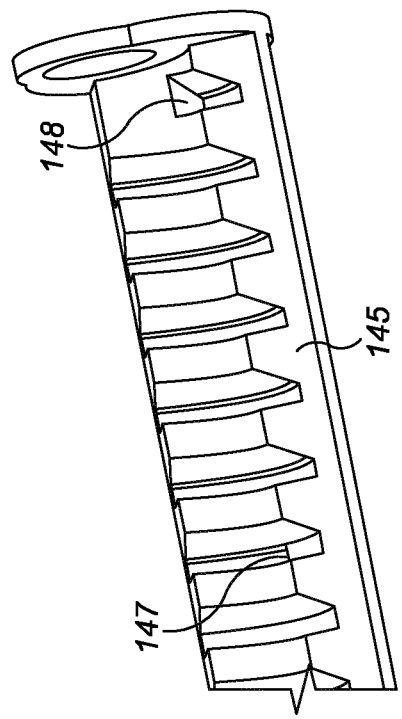
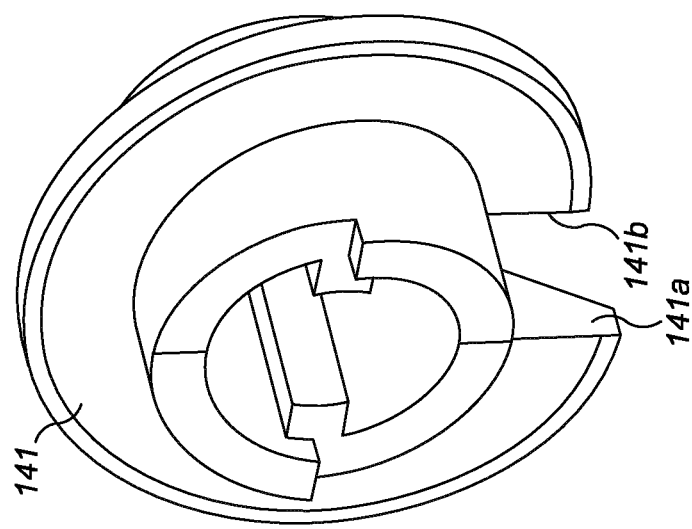
FIG. 5B
FIG. 5A

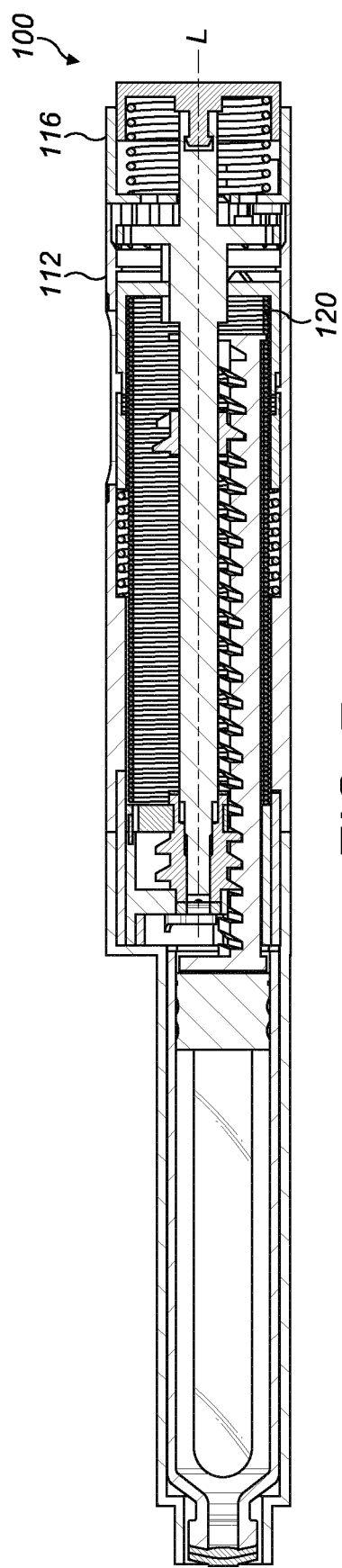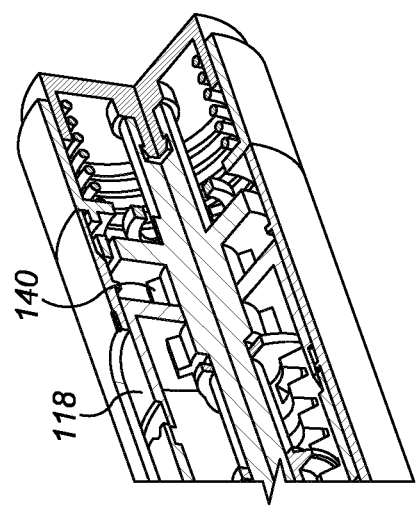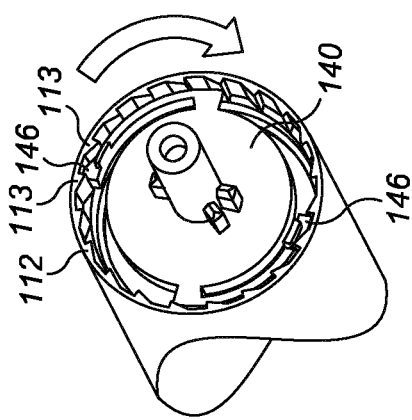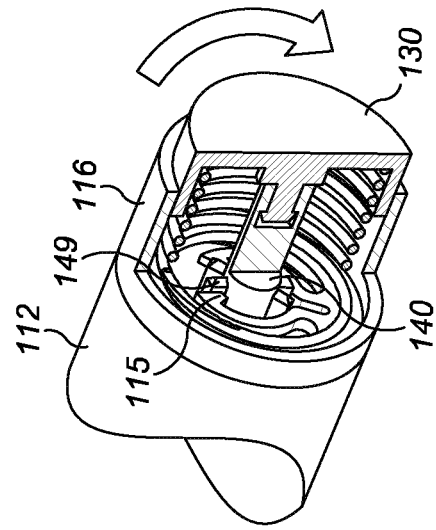

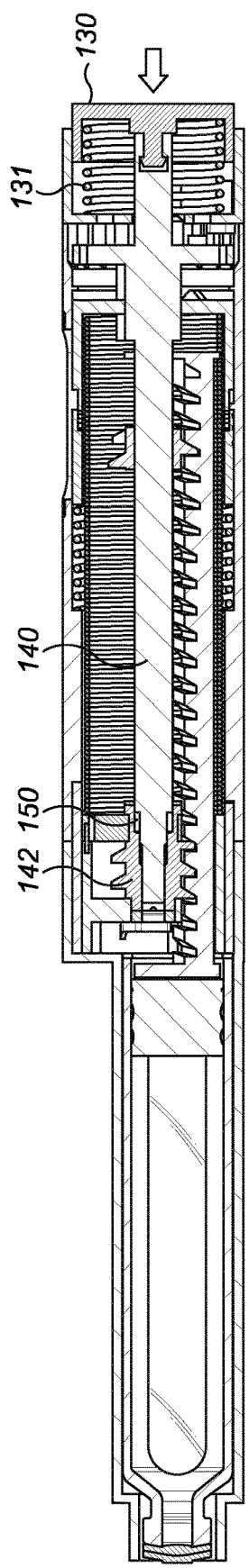
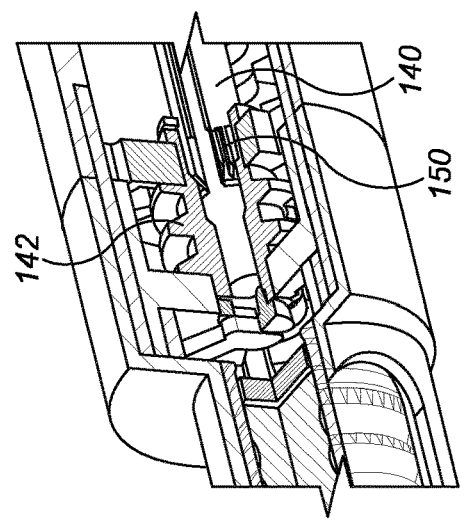
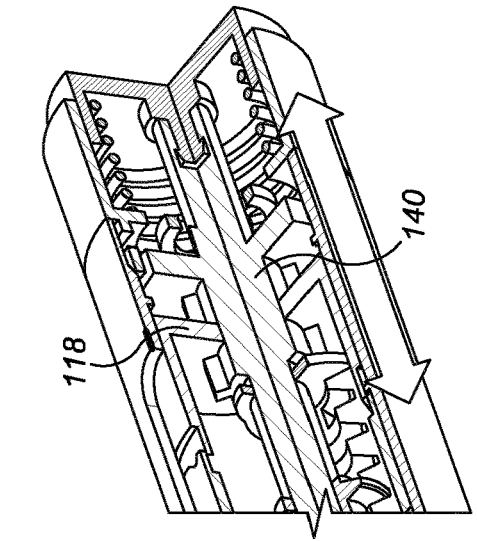
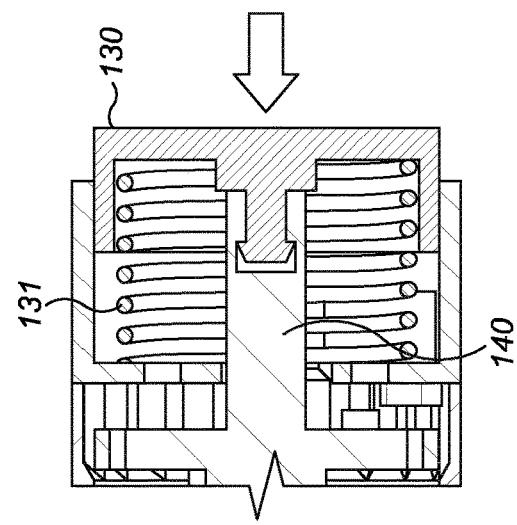

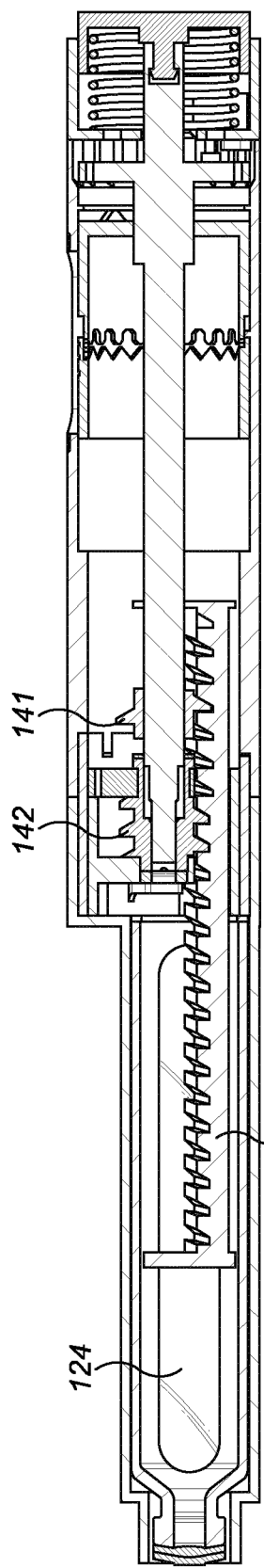
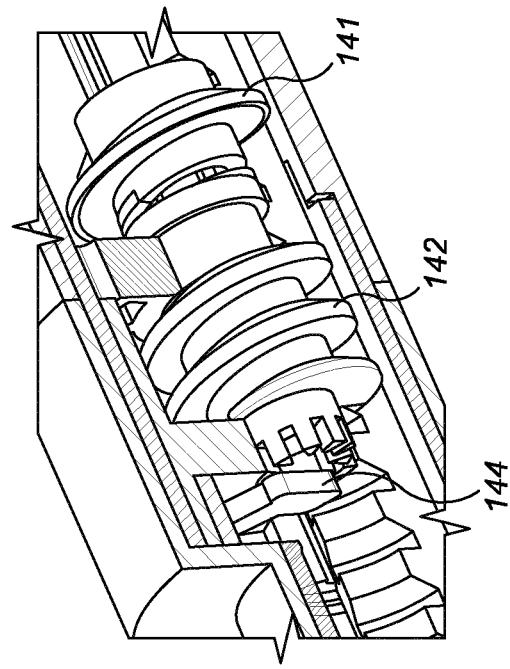
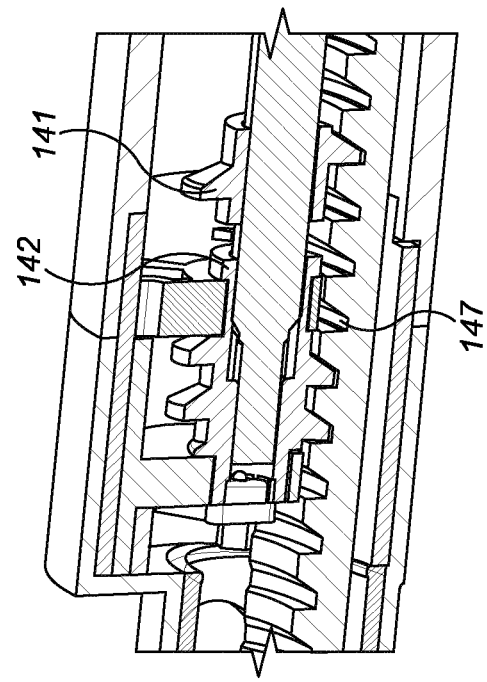
FIG. 14
FIG. 14B
FIG. 14A

| Advancement of dose button (130) in mm | 0mm | 0.9mm | 1.75mm | 3.25mm |
|---|---|---|---|---|
| Hold Ratchet (Housing ramp 111 / Ratchet Arms (146)) | | | | |
| Over torque ratchet (drive shaft splines (149)/dose selector pawl (115)) | | | | |
| Worm Gear Clutch (150) | | | | |
| Worm Gear Rotational Lock (144) | | | | |

Not Engaged | Partially Engaged | Fully Engaged

FIG. 15

DOSE DELIVERY MECHANISM

CROSS-REFERENCE TO RELATED APPLICATIONS

This application is the National Stage of International Patent Application No. PCT/EP2017/072772, filed Sep. 11, 2017, which claims priority from Great Britain Patent Application No. 1615446.0 filed Sep. 12, 2016, the entire contents of both of which applications are incorporated herein by reference.

This disclosure relates to the field of a dose delivery mechanism for an injection device, preferably a reusable pen-injector injection device for injecting a selected dose of medicament.

BACKGROUND

Pen-injector injection devices are well known and an example is shown in WO2015/032780. At the centre of the injection device is a longitudinally-extending lead screw, around which the other components are concentrically arranged about a longitudinal axis extending through the lead screw, the medicament cartridge and out to the injection site. This concentric arrangement, about a single longitudinal axis, is highly desirable in order that maximum use is made of the limited space for the internal components of the injection device. As can be seen from the cross-sectional views in WO2015/032780, the available internal space for any additional components in a pen-injector injection device is very limited indeed. Another example of an injection device with all of its components concentrically arranged about a longitudinal axis is shown schematically in FIG. 1.

A further advantage of the concentric arrangement of the internal components is to ensure that the injection device is well-balanced, during use, when its internal components are subjected to substantial mechanical forces. The handling properties and user-experience of injection devices are critical factors in their design.

U.S. Pat. No. 7,828,779 describes an injection device having a reservoir module 10 connected to a dosing and activating module 20. The reservoir module 10 is arranged about a longitudinal axis L, which is also the translational axis of the piston which displaces medicament from the reservoir.

BRIEF SUMMARY OF THE DISCLOSURE

In accordance with an aspect of the present invention there is provided an injection device comprising:
 a. a housing having a first longitudinal axis;
 b. a medicament cartridge holder;
 c. a plunger element for ejecting a dose of medicament from the injection device, and
 d. a drive assembly, including a drive shaft arranged concentrically about said first longitudinal axis, the drive assembly capable of providing an axial force to said plunger element for ejecting a dose of medicament from the injection device;
 wherein said medicament cartridge holder and said plunger element are arranged around a second longitudinal axis which is substantially parallel to but offset from the first longitudinal axis.

By having some of the components located about a second longitudinal axis which is offset from the longitudinal axis of the housing, additional internal space is created within the device. Additional components, for example components for e-health telematics could be incorporated into the injection device.

In certain embodiments, the drive assembly comprises a rotational to axial coupling, where the drive assembly is rotationally drivable by a torsion spring and is arranged to provide an axial force for ejecting the dose from the injection device.

In certain embodiments, the drive assembly further comprises a worm gear engaged in a rack wherein rotation of said worm gear causes the rack to advance axially forward or backward with respect to said worm gear. The forward advancing rack provides the axial force for ejecting medicament from the injection device. The worm gear may be arranged around said first longitudinal axis and said rack may be arranged around said second longitudinal axis.

In certain embodiments, the drive assembly further comprises a worm gear rotational lock engageable with the worm gear, preferably in a forward end thereof, so as to substantially prevent rotation of the worm gear. The worm gear rotational lock may be disengageable from the forward end of the worm gear by being pushed axially forward by the drive shaft.

In certain embodiments, the drive assembly further comprises means engageable between the drive shaft and the worm gear and which, when engaged, rotationally lock the drive shaft and worm gear together. Preferably, the means is a clutch which may comprise splines. In an embodiment, said means is engageable before said worm gear rotatational lock is disengaged.

The injection device may further comprise a medicament cartridge. Medicament may be contained in the medicament cartridge. In certain embodiments, the medicament may be selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

BRIEF DESCRIPTION OF THE DRAWINGS

Embodiments of the invention are further described hereinafter, by way of example only, with reference to the accompanying drawings, in which:

FIG. 5A is a perspective view showing further detail of the dose limit nut;

FIG. 5B is a perspective view showing further detail of part of the plunger rack;

FIGS. 7 and 7A-7C illustrate incrementing the dose;

FIGS. 11,11A-11C, 12 and 12A-12B illustrate dose delivery;

FIGS. 14 and 14A-14E illustrate last dose protection;

FIG. 15 is a diagrammatic summary of the key engagement points of the components of the injection device of FIG. 4, at four stages of dose delivery;

DETAILED DESCRIPTION

Figure 1:
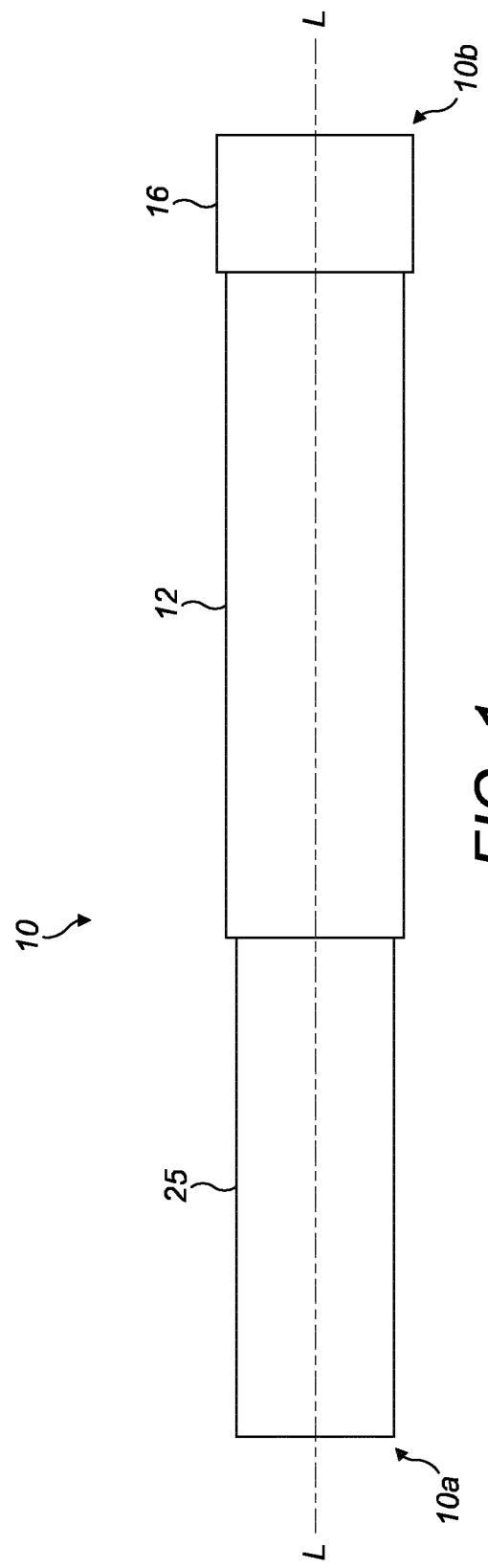
FIG. 1 (PRIOR ART) is a schematic view of a pen-injector injection device having a longitudinal axis L.

In the present disclosure, the following terms may be understood in view of the below explanations:

The term "injection device" may refer to a device intended for the injection of a medicament to the body and includes devices configured for various delivery methods, such as intradermal, subcutaneous, intramuscular, intravenous, intraosseous, intraperitoneal, intrathecal, epidural, intracardiac, intraarticular, intracavernous, and intravitreal, which may include via a cannula, catheter or similar device. Injection device includes syringes of all types, devices that contain said syringes such as auto-injectors, pen-injectors, patch injectors and other similar devices.

The term "pen-injector" may include any device configured to deliver a dose of a medicament from a cartridge.

The term "user" may refer to a medical practitioner, end user or other user associated therewith.

The term "coupling" may refer to a connection between components (not necessarily a direct connection; there may be intermediate components therebetween) that enables a force to be transmitted between the components.

The term "a rotational coupling" may refer to a coupling which enables a rotational force to be transmitted between the components.

The term "operatively connectable" may refer to at least two individual components which are releasably connectable together in such a way that the individual components can work together, for example wherein rotation of one of the individual components effects rotation of all of the operatively connected components.

The term "dose selector" may refer to a component or components which, when actuated by a user, enable a dose of medicament to be selected.

The term "dose indicator" may refer to a component or components which provide a display or indication to the user of the selected dose of medicament.

The term "splines" may refer to one or more ridges, ribs or other protrusions on one component which engage in corresponding grooves or the like on a second component to connect the two components together.

The term "a splined connection" may refer to a connection effected by one or more splines.

The term "forward" or "forwards" may refer to a direction towards the end of the injection device from which medicament is expelled.

The term "backward", "backwards", "rearwards" or "rearwardly" may refer to a direction away from the end of the injection device from which medicament is expelled.

The term "drive assembly" may refer to an assembly of components capable of using a driving force from, for example, a spring, to eject medicament from an injection device.

The term "backlash" may refer to a clearance caused by a gap between mechanical components.

The term "medicament" may include a substance in liquid or gas form. The medicament may be selected from the group comprising of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

When referring to the injection device, the term "containing the medicament" may refer to the medicament being contained within a suitable medicament container, such as a pre-filled syringe or cartridge, within the injection device.

The term "a force path" may refer to a path between two or more coupled components via which a force can be transmitted between the components. A force path may be "interrupted" if there is a gap between the two or more components, i.e. if they are no longer coupled. Transmission of force between coupled components may be "held back" for example by a ratchet arrangement, but in such a case the force path is not "interrupted".

The term "a clutch" may refer to a component or feature suitable for operatively connecting two component parts either by a positive fit e.g. with teeth, splines, grooves or the like suitable for engaging and disengaging each other, or by a non-positive (e.g. frictional) connection or a combination thereof. Disengaging the clutch may interrupt a force path between two or more coupled components.

The term "plunger element" may refer to a piston, plunger, plunger rack or other component which moves axially forward during dose delivery causing medicament to be expelled from the injection device, for example by pushing a stopper into a cartridge of medicament. The term "plunger element" does not include the components which provide axial force to the plunger element.

Description of a First Example Embodiment

A prior art injection device 10 is shown in FIG. 1. The injection device 10 is configured to deliver a dose of medicament and extends along a longitudinal axis L between a front end 10a and a rear end 10b of the injection device 10. All of the components of the injection device 10 are arranged about the longitudinal axis L. The injection device 10 has a housing 12 and a needle (not shown) can be attached to the front end 10a. A dose selector 16 is provided at the rear end 10b and is arranged to permit the selection of a desired dose of medicament for delivery through the needle into an injection site. A medicament cartridge holder 25 for holding a cartridge from which medicament can be dispensed is located at the front end 10a of the injection device 10.

Figure 2:
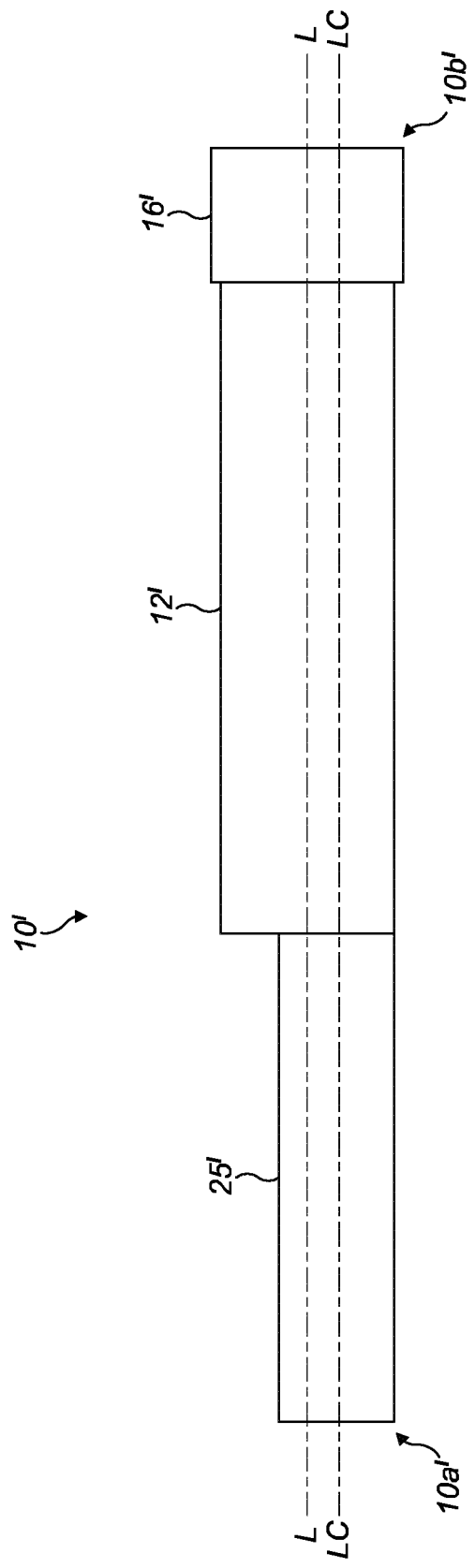
FIG. 2 is a schematic view of an injection device according to an embodiment of the invention.

FIG. 2 shows an injection device 10' according to an embodiment of the invention. The injection device 10' is configured to deliver a dose of medicament and has a front end 10a' and a rear end 10b'. A needle (not shown) can be attached to the front end 10a'. A dose selector 16' is provided at the rear end 10b' and is arranged to permit the selection of a desired dose of medicament for delivery through the needle into an injection site.

The injection device 10' comprises a housing 12' which extends along a longitudinal axis L. A medicament cartridge holder 25' for holding a cartridge from which medicament can be dispensed is located at the front end 10a' of the injection device 10'. The medicament cartridge holder 25' is arranged around a second longitudinal axis Lc wherein the two longitudinal axes L and Lc are substantially parallel but offset from one another. The medicament cartridge holder 25' may be generally symmetrical around axis Lc. The housing 12' may be generally symmetrical around axis L.

Figure 3:
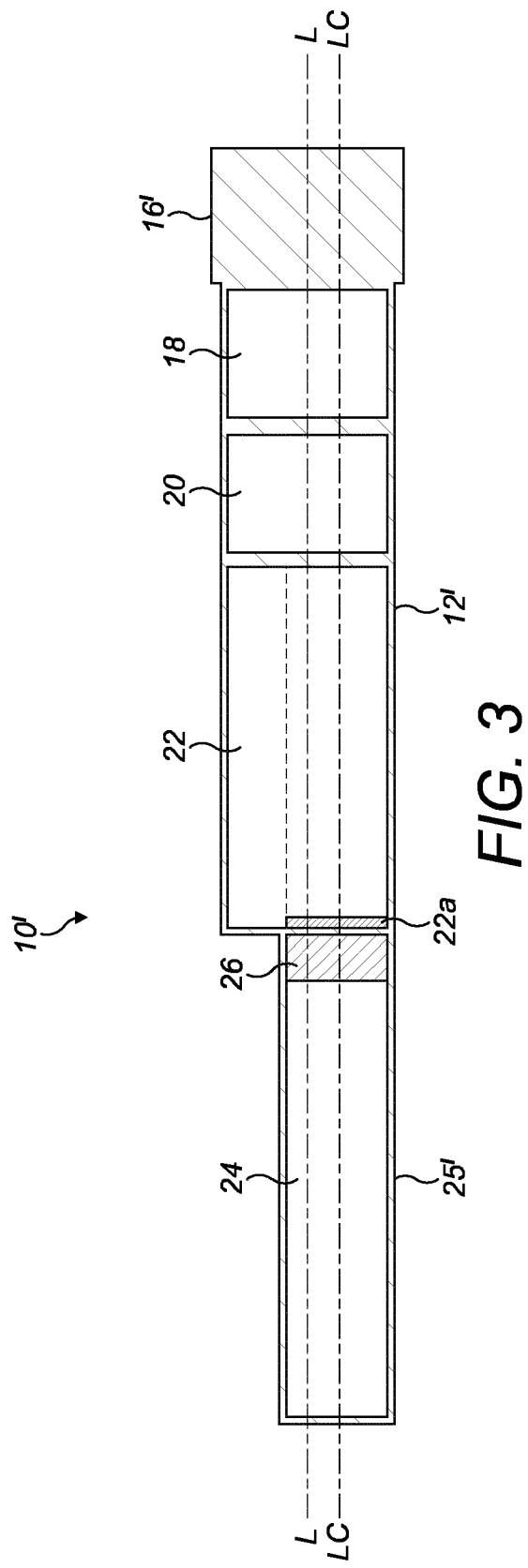
FIG. 3 is a schematic cross sectional view of selected components of the injection device of FIG. 2.

Referring to FIG. 3, a dose indicator 18 is disposed within the housing 12' and displays reference indicia, such as numbers or symbols, to indicate the level of dose selected by the dose selector 16'. The dose indicator 18 is preferably arranged about the longitudinal axis L.

A drive spring 20 is provided which can be charged by the application of force to elastically deform the spring 20, and the resulting elastic energy is stored by the spring 20 (i.e. it is prevented from elastically relaxing during a storage phase). Therefore, charging the spring 20 involves increasing the energy stored by the spring 20. The spring is preferably arranged about the longitudinal axis L.

The spring 20 is coupled to a drive assembly 22 and is arranged to provide a driving force thereto when energy stored by the spring 20 is released. The drive assembly 22 acts on a plunger element 22a to expel medicament from a medicament cartridge 24 having a barrel and a stopper 26 moveable in the barrel. In such embodiments, the plunger element 22a may act to move the stopper 26 so as to expel medicament through an opening in the barrel. In certain embodiments, the medicament cartridge 24 is connected to a needle.

At least part of the drive assembly 22 is arranged about longitudinal axis L. However, plunger element 22a which acts on the stopper 26, is arranged about longitudinal axis Lc.

Therefore, as can be seen in FIG. 3, the medicament cartridge holder 25', any medicament cartridge 24 held therein and the plunger element 22a is arranged about longitudinal axis Lc which is offset from the longitudinal axis L of the housing 12'.

Description of Second Example Embodiment

A further, non-limiting, embodiment of an injection device according to the present invention is illustrated in FIGS. 4-19B.

Figure 4:
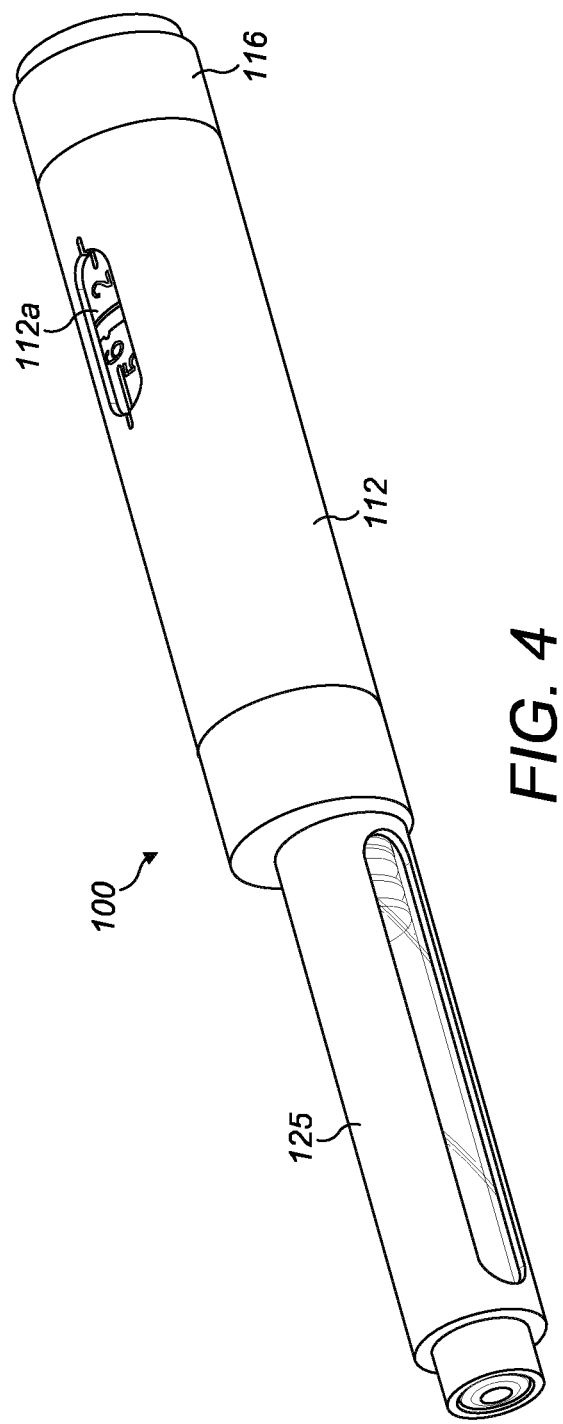
FIG. 4 is a perspective view of another embodiment of the injection device.
Figure 5:
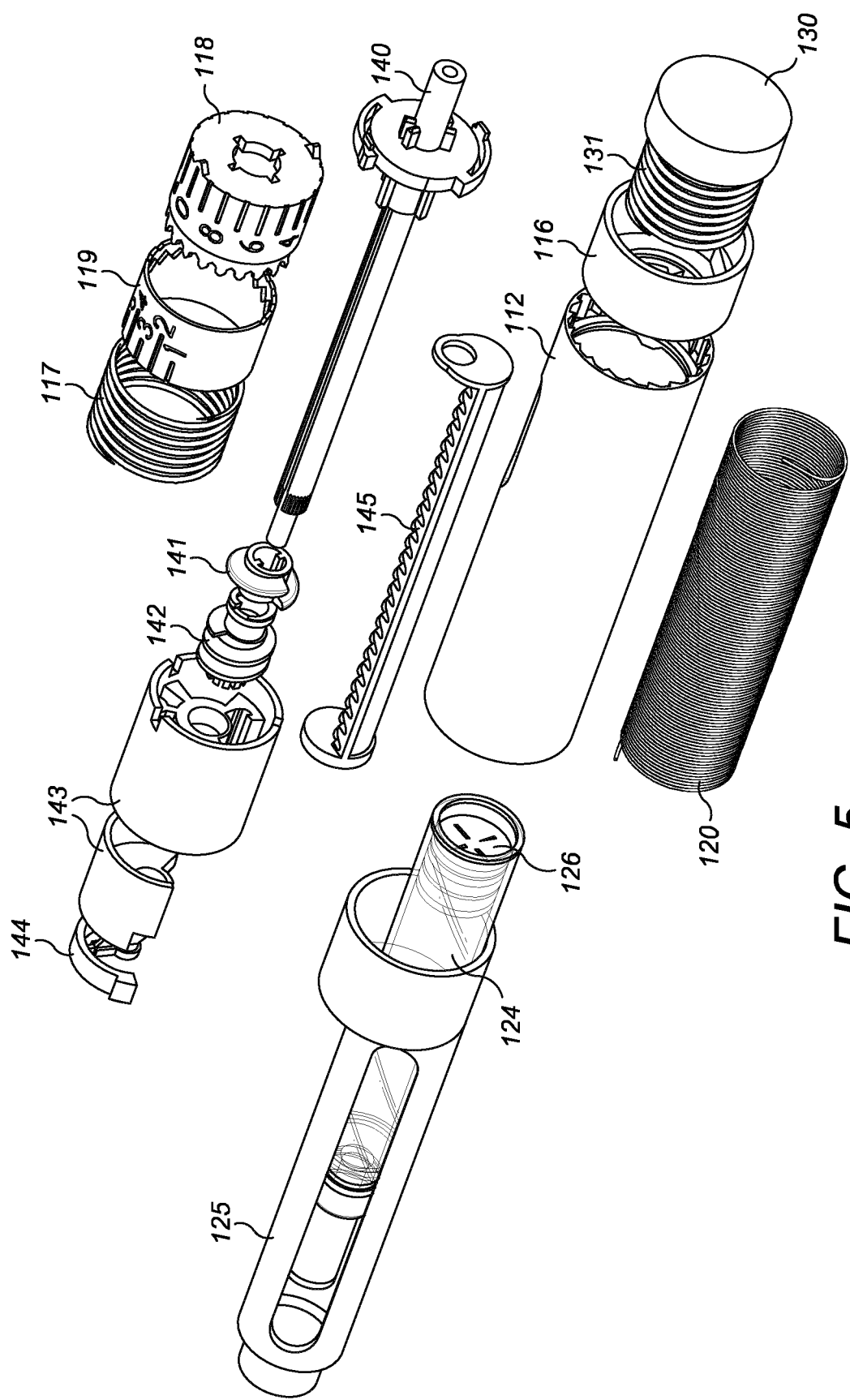
FIG. 5 is an exploded view of the injection device of FIG. 4.
Figure 6:
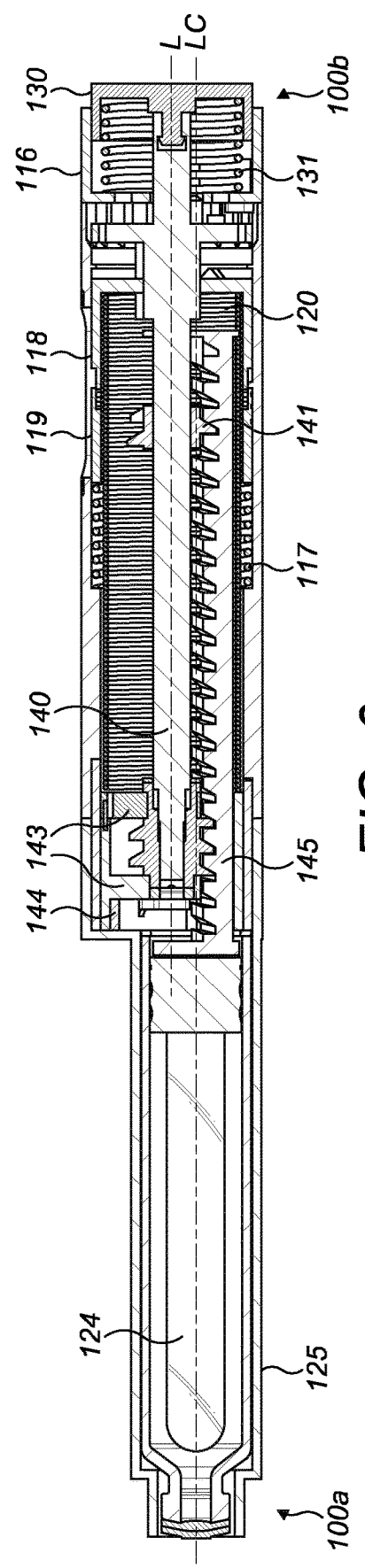
FIG. 6 is a cross-sectional view of the injection device of FIG. 4.

Referring to FIGS. 4-6, the injection device 100 includes a housing 112, a dose selector 116, a dose button 130 and dose button spring 131, a units wheel 118, a tens wheel 119, a dose indicator spring 117, a drive shaft 140, a drive spring 120, a dose limit nut 141, a worm gear 142, a worm gear support 143 and a worm gear rotational lock 144, all located concentrically about a common longitudinal axis L. The axis L extends between a front end 100a and a rear end 100b of the injection device 100.

The injection device 100 has a medicament cartridge 124 supported in a cartridge holder 125 at the front end 100a of the injection device 100. The cartridge 124 is sealed by an axially-moveable cartridge stopper 126 at its rear end. The cartridge and cartridge holder are located concentrically about a second longitudinal axis Lc, such that the cartridge is offset from the main housing 112, with L and Lc offset from one another as shown in FIG. 6.

Figure 8:
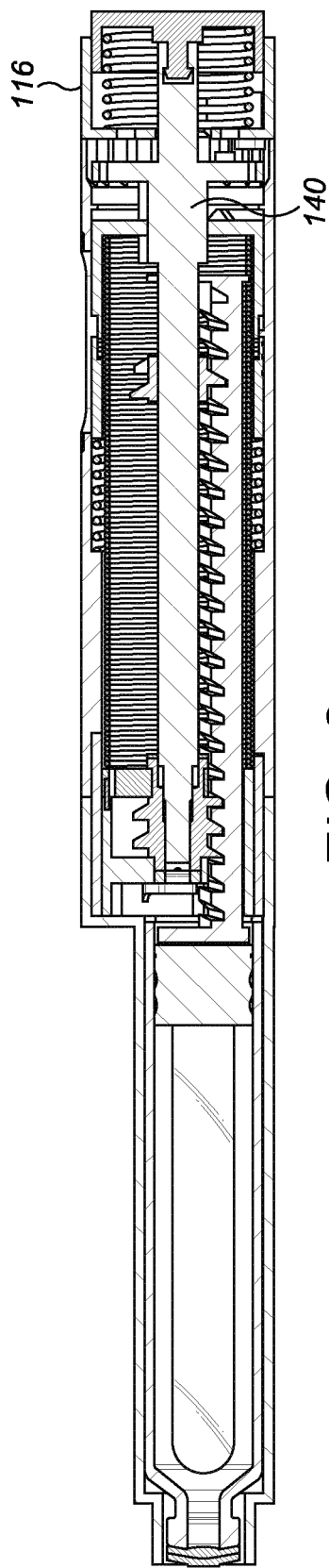
FIGS. 8, 8A and 8B illustrate decrementing the dose.
Figure 8B:
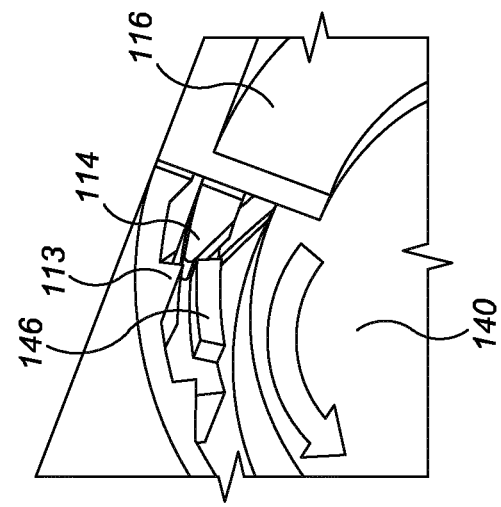

The dose button 130 is biased rearwardly by the dose button spring 131. The dose selector 116 is provided at the rear end 100b of the injection device 100 and is arranged to permit the selection of a desired dose of medicament for delivery from the medicament cartridge 124 into an injection site. The dose selector 116 is axially constrained with respect to the housing 112 but is rotatable with respect thereto, about axis L. The dose selector 116 is rotationally coupled to the drive shaft 140 via pawl features 115, visible in FIG. 7A, which engage splines 149 on the drive shaft 140. The housing 112 is provided with teeth 113 (visible in FIG. 7B) on an inside surface thereof for engaging ratchet arms 146 on the drive shaft 140. Tabs 114 on the dose selector 116 are capable of depressing the drive shaft ratchet arms 146 when required, as shown in FIG. 8B. The housing 112 is also provided with ramp features 111 (visible in FIG. 12A) which facilitate disengagement of the ratchet arms 146 from the inside surface of the housing 112 when required.

A dose indicator is disposed within the housing 112 and displays reference indicia, such as numbers or symbols, to indicate the level of dose selected by the dose selector 116. The housing 112 includes an aperture 112a through which the dose indicator is visible. The dose indicator comprises the units wheel 118 for displaying units and the tens wheel 119 for displaying tens. The units wheel 118 is selectively engageable with the tens wheel to increment the tens wheel each time the units wheel moves through units 0 to 9. The units wheel 118 is rotationally coupled to the drive shaft 140.

As with the first embodiment, described with reference to FIGS. 1-3, biasing means in the form of dose indicator spring 117 biases the units wheel 118 and tens wheel 119 axially rearwardly in the housing.

The housing 112 has features on an inside surface thereof for engaging with the units wheel 118 and the tens wheel 119.

An internal surface of the housing 112 is provided with a tens housing feature 108 selectively engageable with the tens wheel 119 to prevent rotation thereof. The tens housing feature comprises one or more axially forwardly extending formations 108 which may be equally spaced around the internal circumference of the housing 112. The formations 108 engage with corresponding axially rearwardly extending formations 119b at the rear of the tens wheel 119. The tens housing feature formations 108 and the tens wheel formations 119b may be teeth, notches, castellations or any other shaped formations that, when engaged together, prevent relative rotation between the tens wheel 119 and the housing 112.

An internal surface of the housing 112 is provided with a units housing feature 107 capable of moving the units wheel axially-forward against said biasing means 117. The units housing feature is an axially forwardly extending formation 107 having a cam surface which can engage with an axially rearwardly extending formation 118b on the units wheel 118 in order to push the units wheel 118 axially forwards.

Teeth 118a on the front end of the units wheel 118 are engageable with correspondingly shaped teeth 119a at the rear end of the tens wheel 119. On the tens wheel 119, the teeth 119a (for engaging the units wheel) and the tens wheel formations 119b (for engaging the housing) may be concentrically arranged around the longitudinal axis of the injection device, with the teeth 119a radially inward of the formations 119b.

The drive spring 120 is a torsion spring which is fixed at one end with respect to the housing 112 and rotationally coupled at its other end to the drive shaft 140 via the units wheel 118.

A worm gear arrangement is provided which comprises a worm gear 142 meshed with a toothed plunger rack 145 located within the housing 112. During dose delivery, the worm gear 142 drives the plunger rack 145 forward which, in turn, pushes against the cartridge stopper 126 to deliver a dose of medicament. A splined clutch 150 at the forward end of the drive shaft 140 enables the worm gear 142 and drive shaft 140 to be splined together during dose delivery but not during dose setting and this will be described in more detail later. In FIG. 6, the worm gear rotational lock 144 is engaged in the forward end of the worm gear 142, preventing rotation thereof. The worm gear rotational lock 144 is capable of being pushed axially forward by the drive shaft 140 in order to disengage the lock from the worm gear 142.

The dose limit nut 141 is keyed to the drive shaft 140 so that they are rotationally coupled but not axially coupled. The dose limit nut 141 is engaged with the teeth of the plunger rack 145 and can travel axially forward and backward along the plunger rack 145 as the dose is incremented or decremented respectively. The axial range within which the dose limit nut 141 can travel along the plunger rack 145 is determined by dose limit nut endstop features 141a, 141b which can engage features 147, 148 on the plunger rack thread to serve as endstops for the travel of the dose limit nut 141. FIG. 5A shows the maximum dose limit nut endstop feature 141a and the minimum dose limit nut endstop feature 141b in more detail. Endstops 141a, 141b are able to engage features 147, 148 respectively on the plunger rack 145 (FIG. 5B). These features 147, 148 are preferably changes in the depth of or formations on the plunger rack thread, past which the dose limit nut 141 cannot travel. During dose delivery, the dose limit nut 141 rotates about axis L with the drive shaft 140 to which it is keyed, but it does not move axially with respect to the plunger rack 145 with which it is engaged, thus always keeping the dose limit nut 141 within the range defined by the max/min dose endstops 141a, 141b.

The operation of the respective features of the injection device 100 will now be described in more detail below.

Dose Setting—Incrementing the Dose

With the injection device 100 in the configuration shown in FIG. 7, the user grips the dose selector 116 and rotates it clockwise about axis L, with respect to the housing 112, in order to increment the dose and charge the drive spring 120. As the dose selector 116 is turned clockwise, the pawl features 115 engaging the splines 149 on the drive shaft 140 cause the drive shaft 140 to also be driven clockwise, as shown in FIG. 7A.

While the dose is being incremented, the ratchet arms 146 on the drive shaft 140 engage with the teeth 113 on the inside surface of the housing 112 to prevent un-winding by the drive spring 120, as shown in FIG. 7B.

As shown in FIG. 7C, the drive shaft 140 is splined to the units wheel 118 which charges or torques up the drive spring 120. In other words, torque is transferred from the dose selector 116 to the drive spring 120 directly through the dose indicator, i.e. the units wheel 118.

Dose Setting—Decrementing the Dose

Figure 8A:
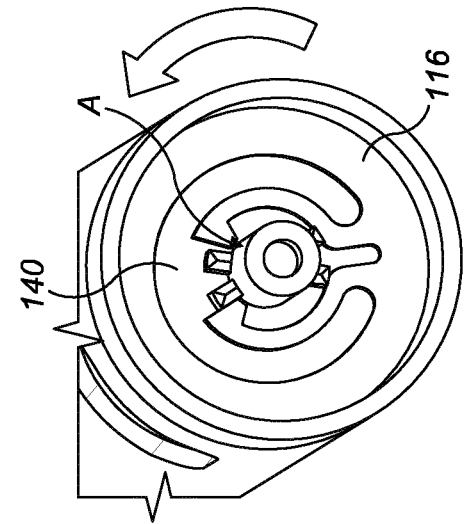

When it is desired to decrement the selected dose, the dose selector 116 is turned anti-clockwise. As shown in FIG. 8A, as the dose selector 116 is turned anti-clockwise, there is a small amount of backlash at point A such that the dose selector 116 can rotate slightly with respect to the drive shaft 140. This small relative movement is sufficient to allow the tabs 114 on the dose selector 116 to depress the drive shaft ratchet arms 146 so that they can click past the housing teeth 113, allowing the drive spring to unwind slightly before the ratchet arms 146 catch again on the next housing tooth 113. This is represented in FIG. 8B. Each decrement preferably equates to 1IU ("international unit") of medicament.

Dose Setting—Maximum/Minimum Dose

Figure 9:
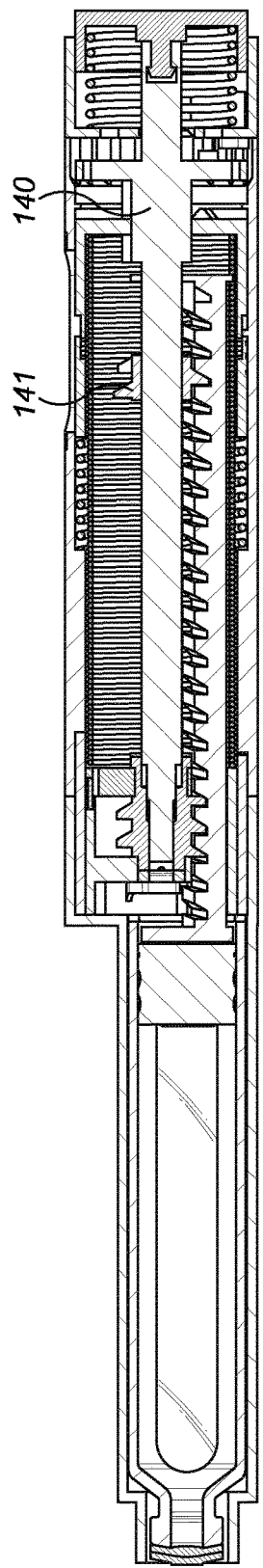
FIGS. 9, and 9A-9D illustrate maximum/minimum dose limiting.
Figure 9C:
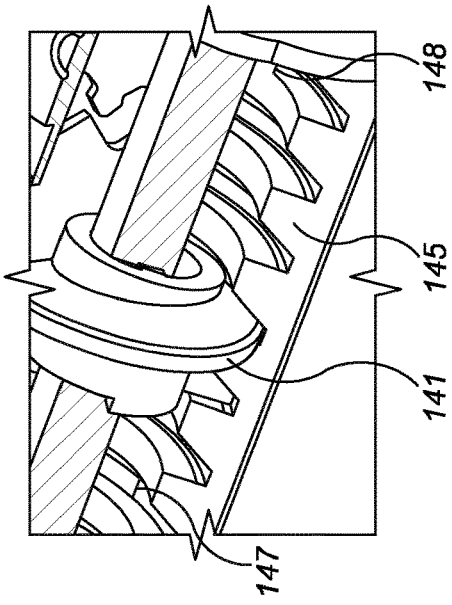
Figure 9B:
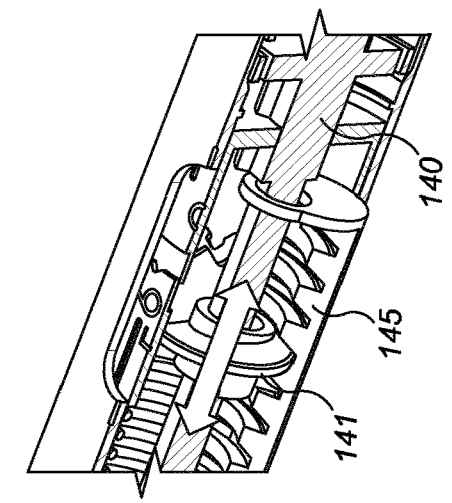
Figure 9A:
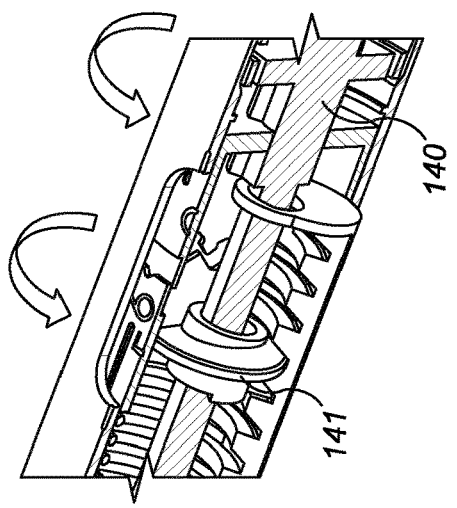
Figure 9D:
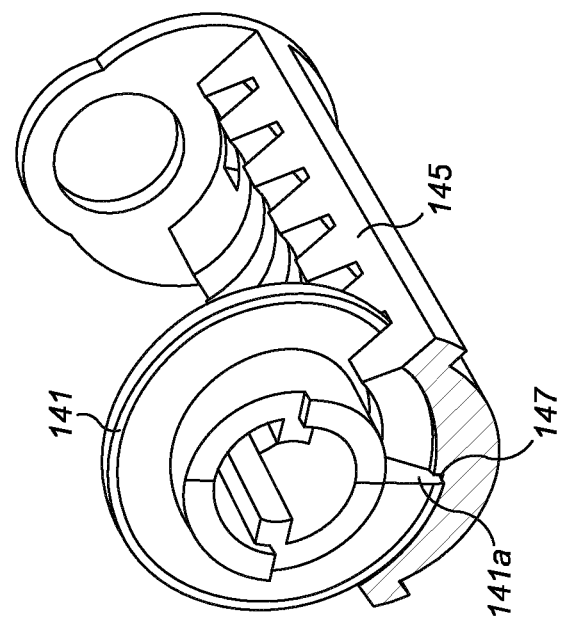

As the drive shaft 140 is rotated during dose setting, the dose limit nut 141, which is keyed to the drive shaft 140, is also rotated (FIG. 9A). The dose limit nut 141 travels forwards when incrementing the dose and rearwards when decrementing the dose (FIG. 9B). The dose limit nut 141 is engaged in the thread of the plunger rack 145. Endstop features 147, 148 are located on the plunger rack 145, past which the dose limit nut 141 cannot travel (FIG. 9C). These endstop features 147, 148 may be changes in the depth of the thread. As shown in FIG. 9D, when the dose limit nut 141 rotates into a position wherein the dose limit nut endstop feature 141a engages feature 147 on the plunger rack 145, further rotation of the dose limit nut 141 is prevented so that a dose of medicament greater than the desired maximum dose of medicament cannot be set. Limiting the travel of the dose limit nut 141 sets the maximum and minimum doses of medicament that can be set during dose setting, preferably 100 IU and 0 IU respectively.

Dose Setting—Over Torque

Figure 10:
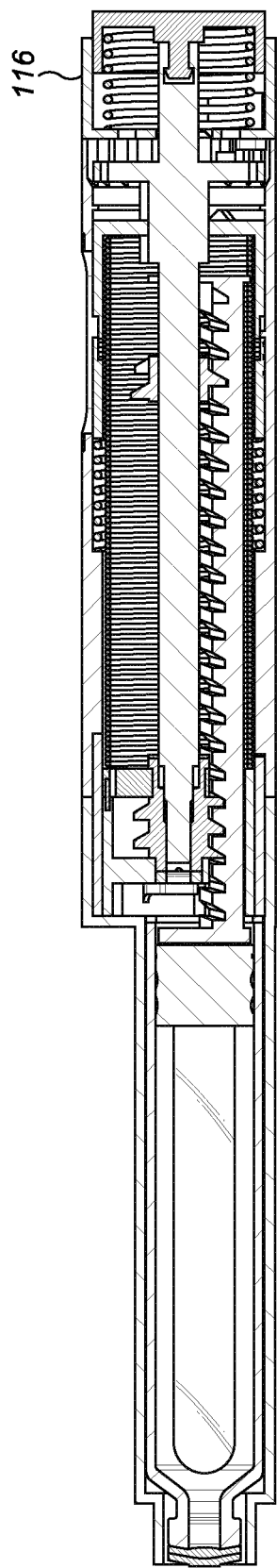
FIGS. 10 and 10A illustrate over-torque protection.
Figure 10A:
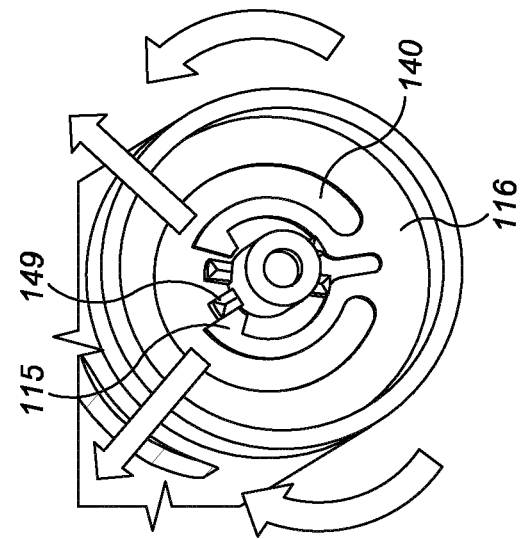

As shown in FIG. 10A, in the event the user applies too much force (over-torque) to the dose selector 116 in either rotational direction, the dose selector pawl features 115 will flex radially outwardly to allow them to skip past splines 149 on the drive shaft 140. Preferably the interfacing surface areas of the pawl features 115 and/or splines 149 act as a cam lever, preferably having a matching angle and/or a defined static and dynamic surface friction at the interface surface. The over-torque for flexing out the dose pawl features 115 to skip past spline 149 is preferably at least 10% higher than the torque required for dialing up (incrementing) or dialing down (decrementing) the dose indicator 18, 118. The dialing up torque can be 30 to 80 Nmm, preferably less than 60 Nmm, more preferably 30 to 50 Nmm. The dialing down torque can be 20 to 60 Nmm, preferably less than 50 Nmm, more preferably 30 to 40 Nmm. The over-torque in the dialing up direction may be different to the over-torque in dialing down direction. The outward flexing force and/or strength of one flexible pawl arm 115 could be lower compared to a second flexible pawl arm.

Figure 16:
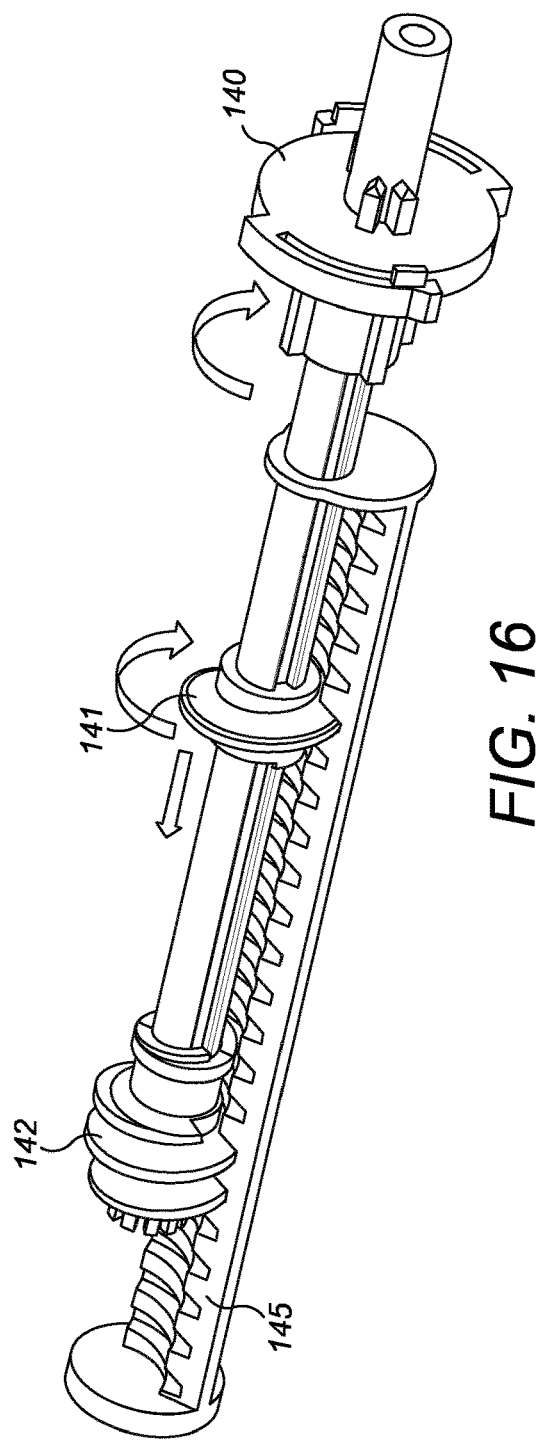
FIG. 16 summarises schematically the mechanical motion of the drive shaft 140, dose limit nut 141, worm gear 142 and plunger rack 145 during dose setting (incrementing the dose)

FIG. 16 summarises schematically the mechanical motion of the drive shaft 140, dose limit nut 141, worm gear 142 and plunger rack 145 during dose setting (incrementing the dose). The drive shaft 140 rotates clockwise. The dose limit nut 141 rotates clockwise and advances forwards with respect to the plunger rack 145.

Dose Delivery

To initiate dose delivery, the user presses the dose button 130 against the bias of the dose button spring 131 as shown in FIG. 11A. This pushes the drive shaft 140 axially forwards. Although the drive shaft 140 is splined to the units wheel 118, it is free to slide axially with respect thereto (FIG. 11B).

Figure 12:
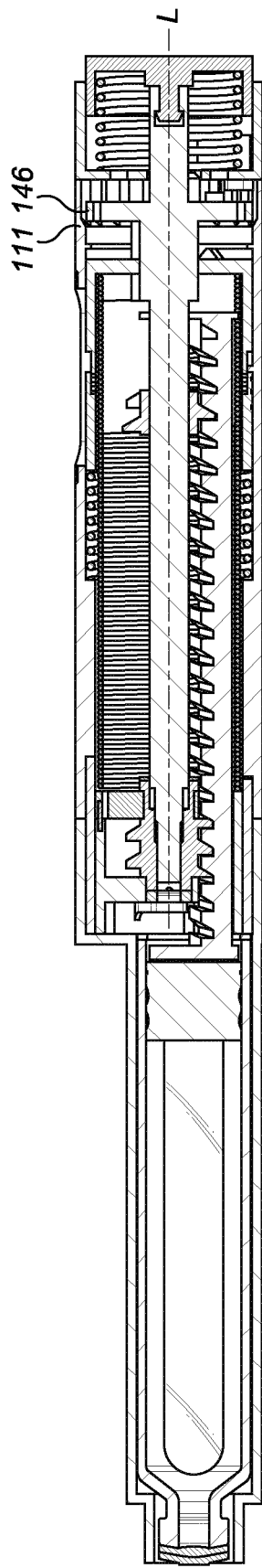
Figure 12B:
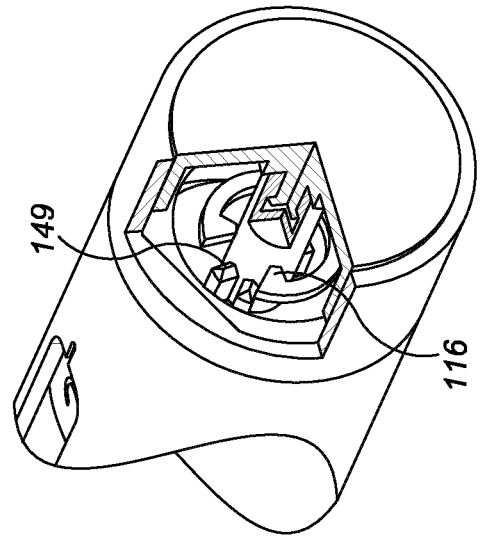
Figure 12A:
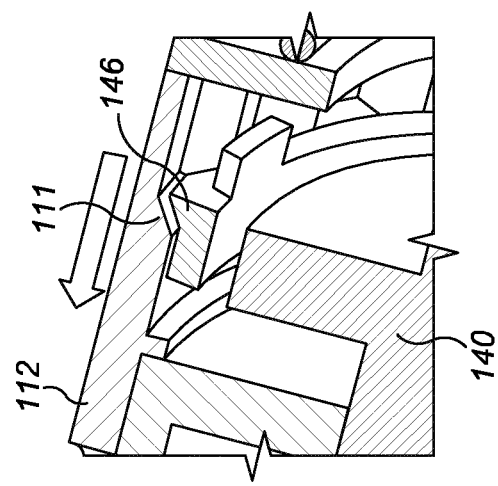

As the drive shaft 140 advances, at its forward end, the splined clutch 150 between the drive shaft and the worm gear 142 engages (FIG. 110, FIG. 15—Worm Gear Clutch 150). Preferably the drive element, in particular the worm gear 142 and the drive shaft 140 engage after 0.5 mm to 1.5 mm advancement of the dose button 130, more preferably after 0.8 mm to 1.2 mm advancement of the dose button 130. Once the clutch 150 has started to engage, the ratchet arms 146 on the drive shaft 140 begin to disengage from the inside surface of the housing 112 aided by ramp features 111 (FIG. 12A, FIG. 15—Hold Ratchet). Preferably the hold ratchet, in particular the ratchet arms 146 on the drive shaft 140 start to disengage from the structured, in particular toothed surface of the housing 112 after 1.5 mm to 2.5 mm advancement of the dose button 130, more preferably after 1.6 mm to 1.9 mm advancement of the dose button 130. Also, as the drive shaft 140 moves forward, the splines 149 coupling the drive shaft 140 to the dose selector 116 disengage (FIG. 12B, FIG. 15—Over torque ratchet). Preferably the over torque ratchet, in particular the drive shaft splines 149 on the drive shaft 140 start to disengage from the dose selector pawls 115 after 1.5 mm to 3.5 mm of advancement of the dose button 130, more preferably after 2 mm to 3 mm advancement of the dose button 130. The dose indicator and drive shaft 140 are now free to rotate about longitudinal axis L.

The drive spring 120 drives the units wheel 118 to rotate about longitudinal axis L. The units wheel 118 drives the drive shaft 140 which drives the worm gear 142.

Figure 17:
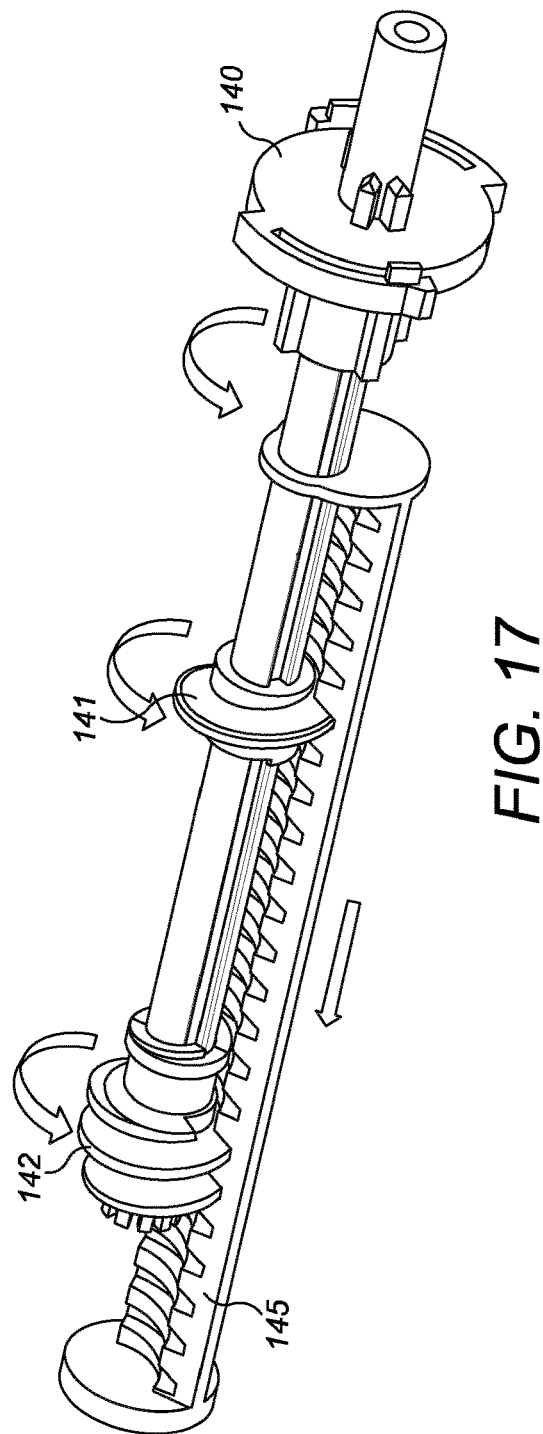
FIG. 17 summarises schematically the mechanical motion of the drive shaft 140, dose limit nut 141, worm gear 142 and plunger rack 145 during dose delivery.

FIG. 17 summarises schematically the mechanical motion of the drive shaft 140, dose limit nut 141, worm gear 142 and plunger rack 145 during dose delivery. The drive shaft 140, dose limit nut 141 and worm gear 142 all rotate anti-clockwise. Only the plunger rack 145 advances forwards. During dose delivery, the dose limit nut 141 rotates with the drive shaft 140 but does not move axially with the plunger rack 145. The dose limit nut 141 and the drive worm gear 142 preferably have the same thread pitch.

The worm gear 142 actuates the plunger rack 145 to move axially forwards causing the cartridge stopper 126 to be driven into the cartridge in order to expel medicament thus delivering the selected dose.

When the dose button 130 is released, the dose button spring 131 returns the dose button 130 and drive shaft 140 to their original starting positions. This axially rearward movement disengages the worm gear clutch 150 and re-engages the drive shaft ratchet arms 146 with the housing 112 thereby stopping dose delivery.

Dose Delivery—Haptic Feedback

Figure 13:
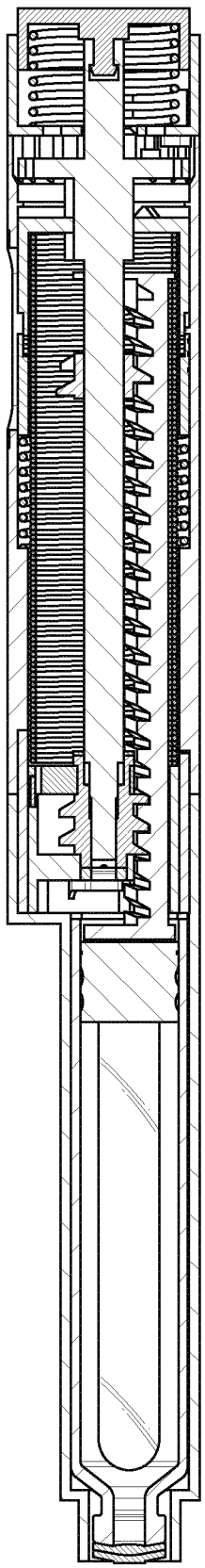
FIGS. 13, 13A and 13B illustrate a haptic feedback feature.
Figures 13A, 13B:
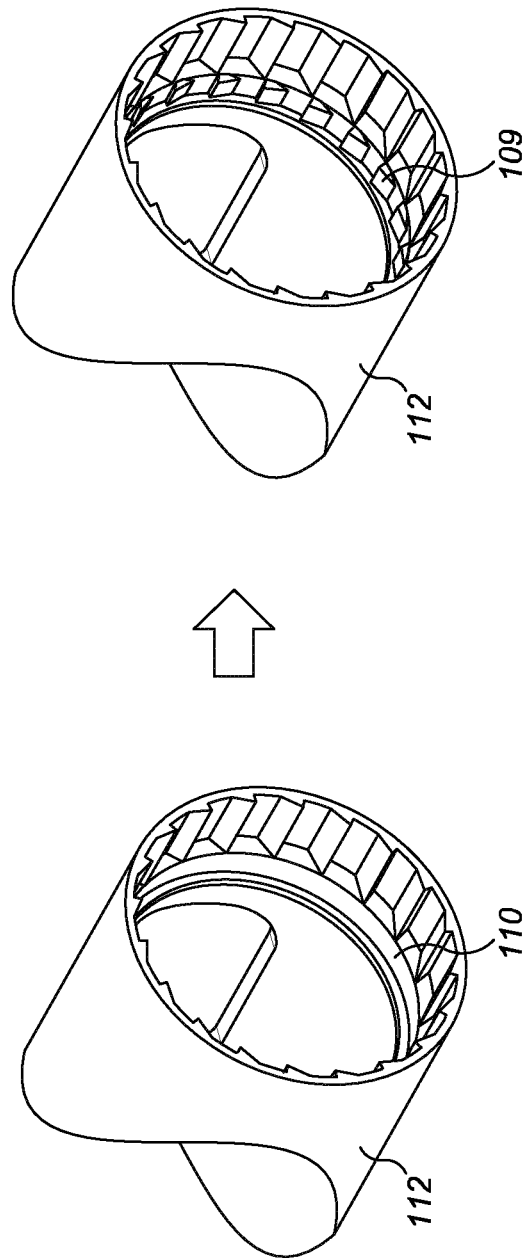

During dose delivery, the drive shaft ratchet arms 146 run (rotationally) on a relatively smooth track 110 on the inside surface of the housing 112 (FIG. 13A). Optionally, this track could be modified to include ridges 109 which would provide audible/haptic feedback to the user during dose delivery (FIG. 13B). The ridges 109 are conveniently placed relatively close to the user's fingers.

Last Dose Protection

When the medicament cartridge 124 is relatively empty, after several doses have already been delivered therefrom, it is undesirable for the user to be able to select a dose that is larger than the available quantity of medicament remaining. Last dose protection is provided to deal with this situation. Conveniently, the last dose protection is provided by the same feature as the max/min dose limiting i.e. the dose limit nut 141.

As shown in FIG. 14, after several doses have been delivered, the plunger rack 145 and dose limit nut 141 have advanced axially forwards such that the dose limit nut 141 is approaching the worm gear 142. When there is less than a predetermined amount (e.g. 100 IU) of medicament available, the worm gear 142 serves as an endstop, stopping the dose limit nut 141 from moving further forwards and before the maximum dose limit feature 147 on the plunger rack 145 is reached (FIG. 14A). Preferably, it is the dose limit nut endstop feature for maximum dose limiting 141a which engages the worm gear 142. If the user tries to increment the dose further, torque is transmitted through the dose limit nut 141 into the worm gear 142, the torque being reacted to by the worm gear rotational lock 144 (FIG. 14B). As such, the worm gear 142 is unable to rotate due to rotational engagement with the rotational lock 144.

Figure 14C:
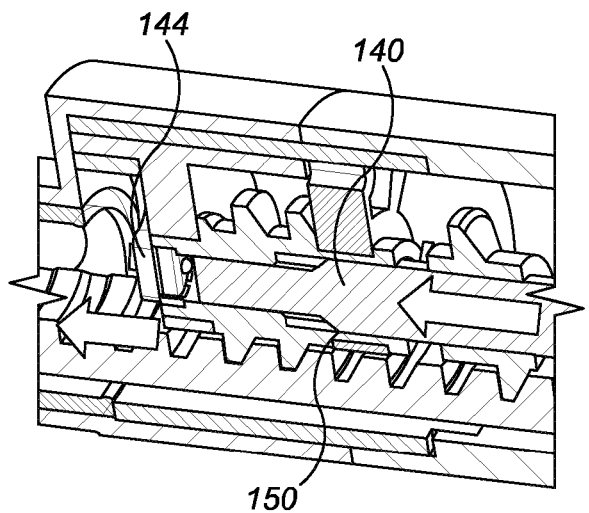
Figure 14D:
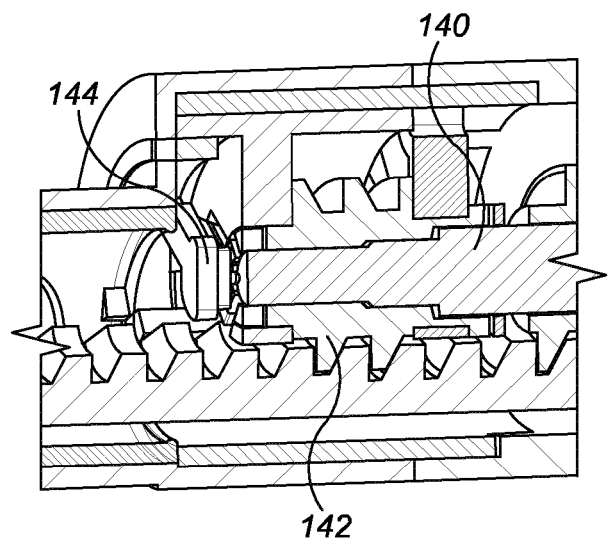
Figure 14E:
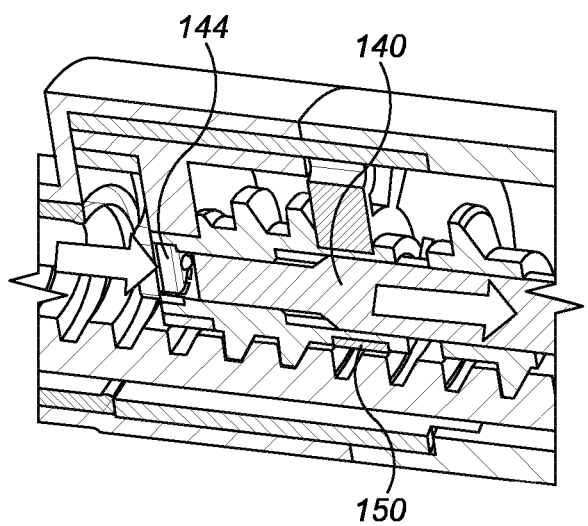

During dose delivery, when the drive shaft 140 is moved axially forwards, the worm gear clutch 150 is engaged before the worm gear rotational lock 144 is disengaged (FIG. 14C). The axially-forward movement of the drive shaft 140 causes its forward end to push the worm gear rotational lock 144 out of the front of the worm gear 142. With the worm gear rotational lock 144 disengaged, the worm gear 142 is free to rotate, driven by the drive shaft 140 (FIG. 14D). Once dose delivery is finished, the drive shaft 140 moves rearwardly. The worm gear rotational lock 144 re-engages, before the worm gear clutch 150 is disengaged (FIG. 14E).

FIG. 15 is a diagrammatic summary of the key engagement points of the injection device components, at four stages of dose delivery.

Dose Display

Figure 18:
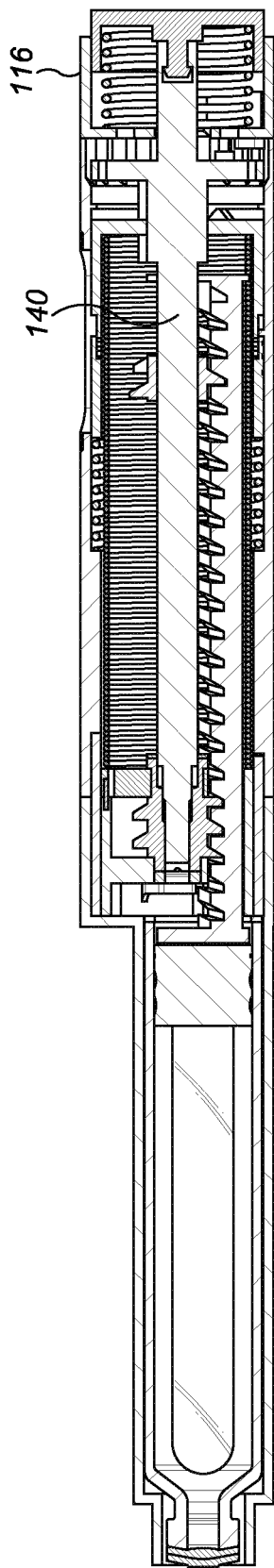
FIGS. 18, 18A and 18B show how the units wheel is incremented.
Figure 18B:
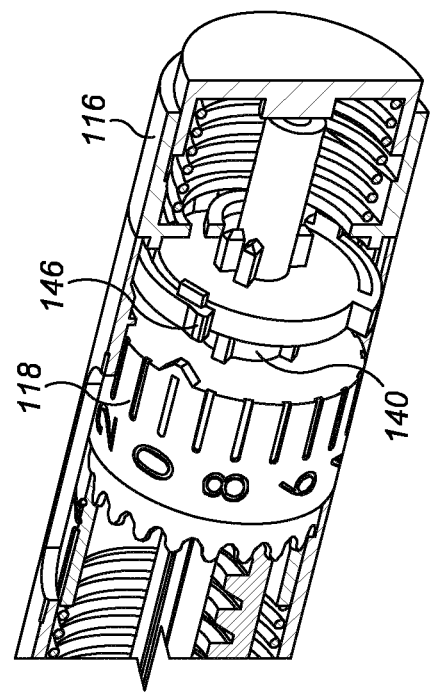
Figure 18A:
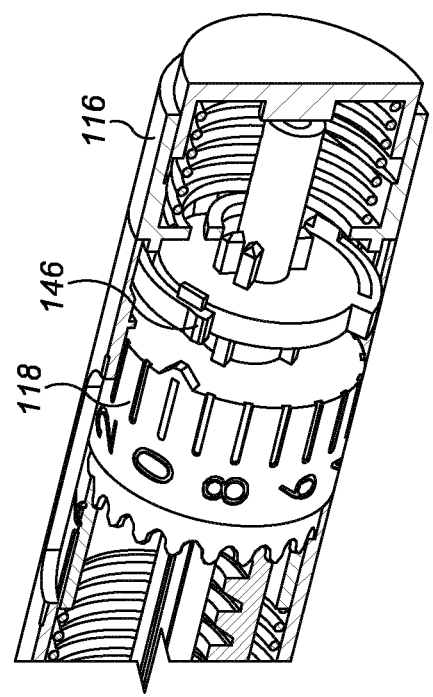

As already described above, during dose selection the user rotates the dose selector 116 which also drives the drive shaft 140 around. Ratchet arms 146 interact with teeth 113 in the housing 112 to prevent unwinding (FIG. 18A). The drive shaft 140 is splined to the units wheel 118 which, as it turns, increments the displayed unit (FIG. 18B).

Figure 19:
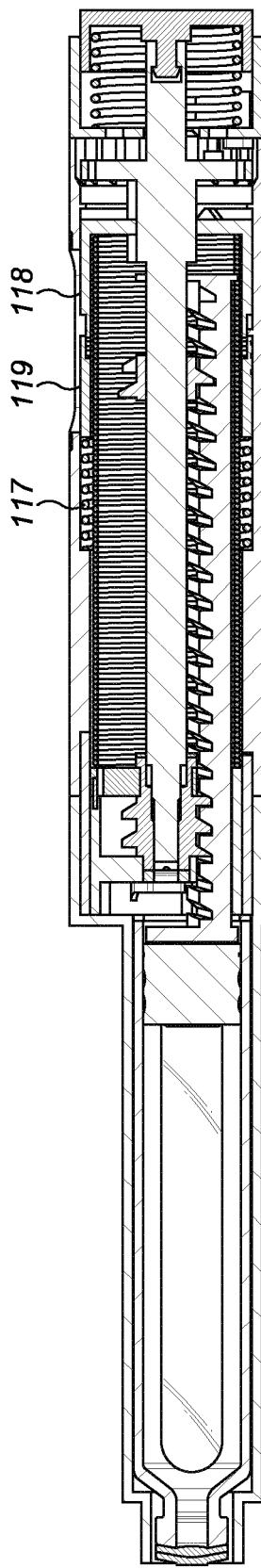
FIGS. 19, 19A and 19B show how the tens wheel is incremented.
Figure 19B:
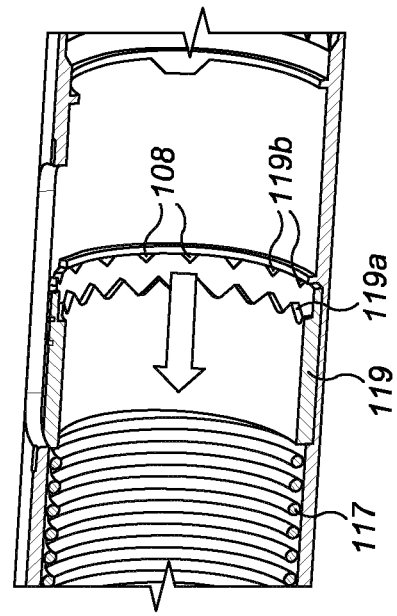
Figure 19A:
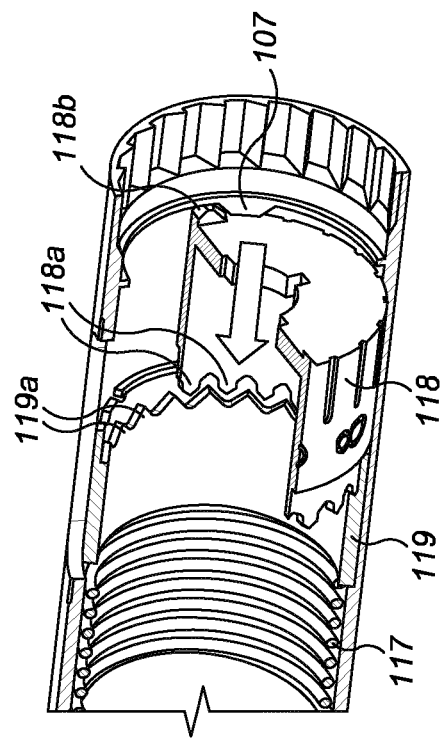

The units wheel 118 and tens wheel 119 are biased rearwardly by dose indicator spring 117. Twice per revolution of the units wheel 118, the units wheel 118 is moved axially forwards by the cam surface of the units housing feature 107 engaging with the formation 118b on the units wheel 118. This axially forward movement causes the teeth 118a of the units wheel 118 to engage with the teeth 119a of the tens wheel 119 (FIG. 19A). Continued forward axial movement of the units wheel 118 pushes the formations 119b of the tens wheel 119 away from the tens housing feature 108, so that the tens wheel 119 is free to rotate with respect to the housing 112, allowing the tens wheel 119 to be driven around by the units wheel 118 by one increment (FIG. 19B).

In a preferred embodiment, the selectable and settable dose range is 1 to 100 IU, with a minimum dose setting of 1 IU, wherein per 360 degree rotation of the dose selector 116, 20 to 30 IU may be set. As the units wheel 118 and tens wheel 119 arrangement permits indication of the set IU dose by two digits, a much larger font size for the indicated dose number is usable, thus the arrangement affords better readability of the set dose and usability of the injection device 10, 100.

As with the first embodiment, described with reference to FIGS. 1-3, the medicament cartridge holder 125, any medicament cartridge 124 held therein and at least part of the drive assembly, namely the plunger rack 145, is arranged about longitudinal axis Lc which is substantially parallel to but offset from the longitudinal axis L of the housing 112.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCE NUMERALS 10, 10' injection device
L longitudinal axis
Lc second longitudinal axis (cartridge holder)
10a, 10a' front end of the device
10b, 10b' rear end of the device
12, 12' housing
16, 16' dose selector
18 dose indicator
20 spring
22 drive assembly
22a drive assembly component
24 medicament cartridge
25, 25' medicament cartridge holder
26 cartridge stopper
100 injection device
L longitudinal axis (housing)
Lc second longitudinal axis (cartridge)
100a front end of the device
100b rear end of the device
107 units housing feature
108 tens housing feature
109 housing ridge features
110 housing smooth inside surface track
111 housing ramps for drive shaft ratchet arms
112 housing
112a aperture in the housing
113 housing teeth
114 tabs
115 dose selector pawl
116 dose selector
117 dose indicator spring
118 units wheel
118a teeth on units wheel (for engaging tens wheel)
118b formation on units wheel (for engaging units housing feature)
119 tens wheel
119a teeth on tens wheel (for engaging units wheel)
119b formations on tens wheel (for engaging tens housing feature)
120 drive spring
124 medicament cartridge
125 cartridge holder
126 cartridge stopper
130 dose button
131 dose button spring
140 drive shaft
141 dose limit nut
141a dose limit nut endstop feature for max dose limiting and last dose limiting
141b dose limit nut endstop feature for min dose limiting
142 worm gear
143 worm gear support
144 worm gear rotational lock
145 plunger rack
146 drive shaft ratchet arms
147 max dose endstop on plunger rack for dose limit nut
148 min dose endstop on plunger rack for dose limit nut
149 drive shaft splines
150 worm gear clutch
A backlash point for over-torque protection

The invention claimed is:

1. An injection device comprising:
   a. a housing having a first longitudinal axis;
   b. a medicament cartridge holder arranged around a second longitudinal axis which is substantially parallel to but offset from the first longitudinal axis; and
   c. a drive assembly including a drive shaft arranged concentrically about said first longitudinal axis, a worm gear engaged in a rack wherein rotation of said worm gear about the first longitudinal axis causes the rack to advance axially forward or backward with respect to said worm gear, and a worm gear rotational lock engageable with the worm gear so as to substantially prevent rotation of the worm gear when engaged with the worm gear.

2. The injection device of claim 1 wherein the drive assembly further comprises a rotational to axial coupling, where the drive assembly is rotationally drivable by a torsion spring and is arranged to provide an axial force for ejecting a dose from the injection device.

3. The injection device of claim 1 wherein said worm gear is arranged around said first longitudinal axis and said rack is arranged around said second longitudinal axis.

4. The injection device of claim 1 wherein the worm gear rotational lock is disengageable from a forward end of the worm gear by being pushed axially forward by the drive shaft.

5. The injection device of claim 1 wherein the drive assembly further comprises means engageable between the drive shaft and the worm gear and which, when engaged, rotationally lock the drive shaft and worm gear together.

6. The injection device of claim 5 wherein the means is a clutch.

7. The injection device of claim 6 wherein the clutch comprises splines.

8. The injection device of claim 5 wherein said means is engageable before said worm gear rotational lock is disengaged.

9. The injection device of claim 1 further comprising a medicament cartridge.

10. The injection device of claim 9 further comprising a medicament contained in the medicament cartridge.

11. The injection device of claim 10, wherein the medicament is selected from the group consisting of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, and in the expression of protective immunity.

12. The injection device of claim 1, wherein the worm gear rotational lock is engageable in a forward end of the worm gear.

13. An injection device comprising:
a. a housing having a first longitudinal axis;
b. a medicament cartridge holder arranged around a second longitudinal axis which is substantially parallel to but offset from the first longitudinal axis; and
c. a drive assembly including a drive shaft arranged concentrically about said first longitudinal axis, a worm gear engaged in a rack wherein rotation of said worm gear about the first longitudinal axis causes the rack to advance axially forward or backward with respect to said worm gear, and a worm gear rotational lock engageable in a forward end of the worm gear.

14. The injection device of claim 13, wherein the drive assembly further comprises a rotational to axial coupling, where the drive assembly is rotationally drivable by a torsion spring and is arranged to provide an axial force for ejecting a dose from the injection device.

15. The injection device of claim 13, wherein said worm gear is arranged around said first longitudinal axis and said rack is arranged around said second longitudinal axis.

16. The injection device of claim 13, wherein the worm gear rotational lock is disengageable from a forward end of the worm gear by being pushed axially forward by the drive shaft.

17. The injection device of claim 13, wherein the drive assembly further comprises a clutch engageable between the drive shaft and the worm gear and which, when engaged, rotationally lock the drive shaft and worm gear together.

18. The injection device of claim 17, wherein the clutch comprises splines.

19. The injection device of claim 17, wherein said clutch is engageable before said worm gear rotational lock is disengaged.

20. The injection device of claim 19, wherein the medicament is selected from the group consisting of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, and in the expression of protective immunity.

21. The injection device of claim 13, further comprising a medicament cartridge including a medicament.

* * * * *